United States Patent
Wolff et al.

(10) Patent No.: US 7,592,499 B2
(45) Date of Patent: Sep. 22, 2009

(54) PROCESS FOR CO-PRODUCING PARA-XYLENE AND STYRENE

(75) Inventors: Luc Wolff, Lyons (FR); Philibert Leflaive, Bures sur Yvette (FR); Alain Methivier, Marly le Roi (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 354 days.

(21) Appl. No.: 10/666,523

(22) Filed: Sep. 22, 2003

(65) Prior Publication Data

US 2005/0038308 A1 Feb. 17, 2005

(30) Foreign Application Priority Data

Sep. 20, 2002 (FR) .................................. 02 11700

(51) Int. Cl.
*C07C 7/00* (2006.01)
(52) U.S. Cl. ...................... 585/805; 585/442; 585/479; 585/822; 585/825; 585/828; 422/222
(58) Field of Classification Search ................. 422/222; 585/442, 479, 805, 828, 822, 825
See application file for complete search history.

(56) References Cited

U.S. PATENT DOCUMENTS

| | | | |
|---|---|---|---|
| 3,306,942 A * | 2/1967 | Lee | 585/442 |
| 3,813,452 A * | 5/1974 | Bieser | 585/479 |
| 5,401,476 A | 3/1995 | Hotier et al. | |
| 5,877,385 A | 3/1999 | Norwood et al. | |
| 6,369,287 B1 | 4/2002 | Magne-Drisch et al. | |
| 6,841,714 B2 * | 1/2005 | Leflaive et al. | 585/828 |

FOREIGN PATENT DOCUMENTS

| | | |
|---|---|---|
| EP | 0956899 | 11/1999 |
| FR | 2693187 | 1/1994 |
| FR | 2795069 | 12/2000 |

* cited by examiner

*Primary Examiner*—Glenn Caldarola
*Assistant Examiner*—Prem C. Singh
(74) *Attorney, Agent, or Firm*—Millen, White, Zelano & Branigan, P.C.

(57) ABSTRACT

A process for co-producing para-xylene and styrene from a feed (1) of hydrocarbons containing xylenes and ethylbenzene is described, the process comprising the following succession of steps:
- a step for separating the feed in a simulated moving bed in an adsorption column (6) containing beds of an adsorbent, from which an extract that is rich in para-xylene (7*a*) of at least 99.7% purity and at least one raffinate (7*b*) containing ethylbenzene, ortho-xylene, meta-xylene and a very small quantity of para-xylene is withdrawn;
- a step for dehydrogenating (10) the ethylbenzene contained in the raffinate (7*b*) to styrene;
- at least one step for primary separation of the stream (11) from the dehydrogenation step (10), to eliminate by-products;
- a step for separating the purified mixture (18) derived from the stream (11) containing styrene, unconverted ethylbenzene, meta-xylene and ortho-xylene, from which a stream (21*a*) that is rich in styrene of at least 99.8% purity and a stream (21*b*) containing unconverted ethylbenzene, meta-xylene and ortho-xylene is withdrawn;
- and a step for isomerising the stream (21*b*), the effluent being recycled to the adsorption column (6).

27 Claims, 2 Drawing Sheets

//PROCESS FOR CO-PRODUCING PARA-XYLENE AND STYRENE

PRIOR ART

The invention relates to a process for co-producing para-xylene and styrene of high purity from a stream principally containing aromatic compounds containing eight carbon atoms.

The production of high purity para-xylene by separation by adsorption is well known in the prior art. The market for para-xylene has developed strongly; it principally lies in the production of terephthalic acid, phthalic anhydride and polyethylene terephthalate resins. The prior art describing the production of high purity para-xylene is illustrated in the Applicant's European patent EP-A-0 531 191.

Further, the market for styrene has also developed strongly, since styrene is used as a monomer for the synthesis of polystyrene (PS) and as a copolymer in the syntheses of acrylonitrile-butadiene-styrene (ABS) and styrene-butadiene (SBR).

The production and purification of styrene at a purity that satisfies market demands (>99.8% by weight) has been the concern of several patents. The majority thereof employ three-step processes:

a step for alkylating ethylene onto benzene to produce ethylbenzene;
a step for dehydrogenating ethylbenzene to styrene;
a step for purifying the product leaving the dehydrogenation unit to produce a stream essentially composed of pure styrene and a stream essentially composed of ethylbenzene, which is recycled to a dehydrogenation unit.

U.S. Pat. No. 6,031,143 describes an adaptation of the above layout in which the ethylene used for alkylation is co-produced with styrene in a dehydrogenation unit from ethane, said ethylene then being separated by distillation and recycled to the alkylation unit. The separation step is constituted by a distillation system.

International patent application WO-A-97/18034 employs an ensemble of catalysts that can carry out dehydrogenation of alkyl aromatics to produce unsaturated aromatics.

In fact, the dehydrogenation step and the variety of catalysts that can carry out that reaction are well known. A great deal of study has been carried out to render the dehydrogenation step more economical, since the energy cost for dehydrogenation, an endothermic reaction, is high. U.S. Pat. No. 4,628,136 (corresponding to EP-A-0 226 064) and U.S. Pat. No. 4,774,378 (corresponding to EP-A-0 238 400) disclose processes for producing styrene with substantial adaptation of the dehydrogenation step since the latter is carried out in the presence of steam.

In U.S. Pat. No. 4,628,136, the mixture of steam and ethylbenzene which enters the dehydrogenation reactor with pure steam is successively heated by heat recovery from the condenser of the distillation column acting to separate the styrene from the ethylbenzene, then by heat recovery from the effluent from the dehydrogenation reaction.

U.S. Pat. No. 4,774,378 discloses a process comprising three dehydrogenation reactors, steam acting firstly to heat the reaction effluents from the last two reactors before being mixed with ethylbenzene at the inlet to the first dehydrogenation reactor.

Along with the above basic processes in which styrene is produced directly, there are a certain number of patents describing the recovery of styrene or ethylbenzene as by-products formed during other reactions.

As an example, U.S. Pat. No. 5,877,385 describes a number of layouts for extracting and/or producing and purifying styrene contained in certain streams generated by oil refining, petrochemistry (pyrolysis gasolines) or by treating natural gas. Said streams contain styrene directly or the intermediate that produces styrene, namely ethylbenzene.

The purification techniques described are many in number and extend from simple distillation, azeotropic or extractive distillation, liquid-liquid extraction, formation of a chemical complex, membrane separation, to a combination of several of these techniques.

One particular technique for producing styrene is described in U.S. Pat. No. 5,877,385. It concerns a process for producing styrene from the C8 cut of a reforming stock containing ethylbenzene, ortho-, meta- and para-xylene and substantially free of styrene. That process comprises:

a splitter (distillation column) that can produce an overhead stream that is rich in ethylbenzene containing a portion of the meta- and para-xylene, and a tail stream containing ortho-xylene and the complement of meta- and para-xylene;
sending said overhead flux to a dehydrogenation unit to convert at least a portion of the ethylbenzene to styrene;
sending the stream leaving the dehydrogenation unit to an ensemble of styrene purification units comprising an extractive distillation column operating with a solvent, preferably selected from water and sulpholane, then carrying out a stripping step to recover said solvent, and purifying the styrene on a column.

That patent is based on the production of high purity styrene but does not describe the co-production of para-xylene.

Other patents more specific to the purification of styrene from C8 aromatic hydrocarbon feeds have been described in the prior art.

A liquid-liquid extraction process has been described in U.S. Pat. No. 4,031,153. That patent describes separating styrene from xylene isomers (ortho-, meta-, para-) and ethylbenzene, contained as a mixture in pyrolysis gasolines from the steam cracker, for example, in two steps: a first step comprising two fractionators (in fact distillation columns) disposed in series, the first enabling overhead elimination of ethylbenzene, para- and meta-xylene, with ortho-xylene and styrene being eliminated as a tails product; and the second eliminating heavy compounds containing 9 or more carbon atoms as a tails product; and a second step comprising a liquid-liquid extractor. The solvent used is succinonitrile which is then recovered during a stripping step.

Other steps for purifying styrene by extractive distillation have been described in U.S. Pat. No. 4,959,128 and U.S. Pat. No. 4,966,656. Said techniques are based on the use of compounds of greater or lesser complexity as the extraction agent.

U.S. Pat. No. 4,959,128, which describes the separation of styrene and ethylbenzene, cites nitrated organic products such as adiponitrile, methyl-glutaronitrile or nitrobenzene.

U.S. Pat. No. 4,966,656 discloses a technique for separating styrene and ethylbenzene or ortho-xylene by extractive distillation or azeotropic distillation using esters such as ethyl isovalerate, propyl caproate, butyl propionate or hexyl formate.

U.S. Pat. No. 6,096,941 describes different layouts for purifying the stream from an ethylbenzene dehydrogenation unit. It also describes technological innovations concerning the different distillation columns (column bottom, liquid distributor). While that invention can substantially reduce the column diameter, it should however be noted that, whatever the proposed layout, it is necessary to use two distillation columns and usually three (in addition to the first column of the purification complex which separates benzene/toluene from the styrene/ethylbenzene/xylenes mixture). All of those columns are operated under vacuum to prevent any undesirable polymerization of the styrene.

Two Japanese patents, JP-A-02138137 and JP-A-03020229, respectively disclose the separation of styrene from a C8 aromatic cut by adsorption onto a faujasite type zeolitic adsorbent, and a process for producing styrene comprising a distillation step that can produce 80% by weight ethylbenzene, an ethylbenzene dehydrogenation step and a step for separating styrene by adsorption onto a faujasite, doped with a monovalent metallic cation. In those two patents, there is no mention of the co-production of high purity para-xylene as no information is given regarding the quality of the products obtained.

In view of the prior art, then, to our knowledge there is no technique that can co-produce para-xylene in a purity of at least 99.7% by weight, and styrene in a purity of at least 99.8% by weight. The very frequent presence of ethylbenzene in the feed entering the para-xylene production loop provides the intermediate immediately preceding styrene, i.e. ethylbenzene, while styrene is produced by dehydrogenating ethylbenzene.

The present invention aims to show how, by integrating the production of styrene with a para-xylene production loop, a large synergistic effect is produced that can simplify the styrene manufacturing layout, in particular as the benzene alkylation step is no longer necessary. The process of the invention can also optimize the operation of the isomerisation unit for xylenes and renders easier the operation of the para-xylene separation unit by substantially reducing the quantity of ethylbenzene entering it.

BRIEF SUMMARY OF THE INVENTION

The invention provides a novel process for co-producing very high purity para-xylene and styrene from a hydrocarbon feed containing aromatic C8 hydrocarbons, ethylbenzene and C9 and C10 hydrocarbons (Cn designating a feed essentially comprising hydrocarbons containing n carbon atoms). Para-xylene is obtained in a purity of at least 99.7% by weight and styrene is obtained in a purity of at least 99.8% by weight.

The process is characterized by the use of at least one chromatographic column or adsorption column operating as a simulated moving bed and allowing para-xylene extraction, styrene being extracted by means of at least one second chromatographic column, but also using any other technique selected from simple distillation, azeotropic or extractive distillation, liquid-liquid extraction, the formation of a chemical complex, membrane separation, separation by adsorption or any combination of a plurality of said techniques.

In the remainder of the text, we shall describe the process is a variation characterized in that the styrene is separated using at least one chromatographic column operating as a simulated moving bed. The term "step" designates one or a group of similar operations carried out on a stream at a certain point in the process. The process will be described in its different steps taken in the direction of flow of the stream or products, and the term "first adsorption separation column" designates the simulated moving bed adsorption column from which para-xylene is extracted, and the term "second adsorption separation column" designates the simulated moving bed adsorption column from which styrene is extracted. For simplicity, the remainder of the text will refer to the first separation column and the second separation column.

More generally, the invention concerns a process for co-producing high purity para-xylene and styrene, from a feed containing xylenes, ethylbenzene and C9-C10 hydrocarbons, the process comprising the following steps in succession:

a step for distilling the feed (1) carried out in a distillation column (2) to separate the xylenes, from which an overhead stream (3) comprising the major portion of the meta-xylene, para-xylene, ethylbenzene and at least a portion of the ortho-xylene is withdrawn overhead, and from which a stream (4) containing C9-C10 hydrocarbons and the remainder of the ortho-xylene is extracted from the bottom;

a step for adsorption of the overhead stream (3) in at least one first adsorption column (6) operating as a simulated moving bed and containing a plurality of beds of an adsorbent, preferably interconnected in a closed loop, and having a different selectivity for para-xylene, ethylbenzene, meta-xylene and ortho-xylene, said column comprising at least four operational zones: a zone 1 for desorbing para-xylene located between the injection point for a desorbant (5) and for removing an extract (7a); a zone 2 for desorbing ethylbenzene, ortho-xylene and meta-xylene located between the extract (7a) removal point and that for injecting the adsorption feed (3); a zone 3 for adsorption of para-xylene located between the injection point for the feed (3) and that for withdrawing a raffinate (7b); and a zone 4 between the raffinate (7b) withdrawal point and that for injection of the desorbant (5);

a step for distilling the extract (7a) carried out in at least one distillation column (8a), withdrawing pure para-xylene (9a), preferably at least 99.7% by weight pure from said column (8a), and withdrawing desorbant from said column and recycling it at least in part to the first adsorption column;

a step for distilling the raffinate (7b) in at least one distillation column (8b) and withdrawing the desorbant from the column at least a portion of which is recycled to the first adsorption column, and a distilled raffinate (9b) containing meta-xylene, ortho-xylene and ethylbenzene;

a step for dehydrogenating the distilled raffinate comprising ethylbenzene into an effluent containing styrene, meta-xylene, ortho-xylene, unconverted ethylbenzene and by-products, carried out in at least one dehydrogenation zone (10), during which at least 50% by weight of the ethylbenzene introduced is converted into styrene;

at least one step for eliminating by-products in at least one distillation column to produce a mixture (18) containing a majority of styrene, ethylbenzene, meta-xylene and ortho-xylene;

a step for separating the mixture (18) and withdrawing from said step a first stream (23a) containing at least 99.8% by weight pure styrene and a second stream (23b) containing the majority of meta-xylene and ortho-xylene;

a step for isomerising (24) the second stream (23b), preferably in the liquid phase, in at least one isomerisation zone (24)., and recovering para-xylene (25), ortho-xylene and meta-xylene which is recycled upstream of the feed distillation column (2).

The invention will be better understood from the accompanying Figures in which.

Figure 1:
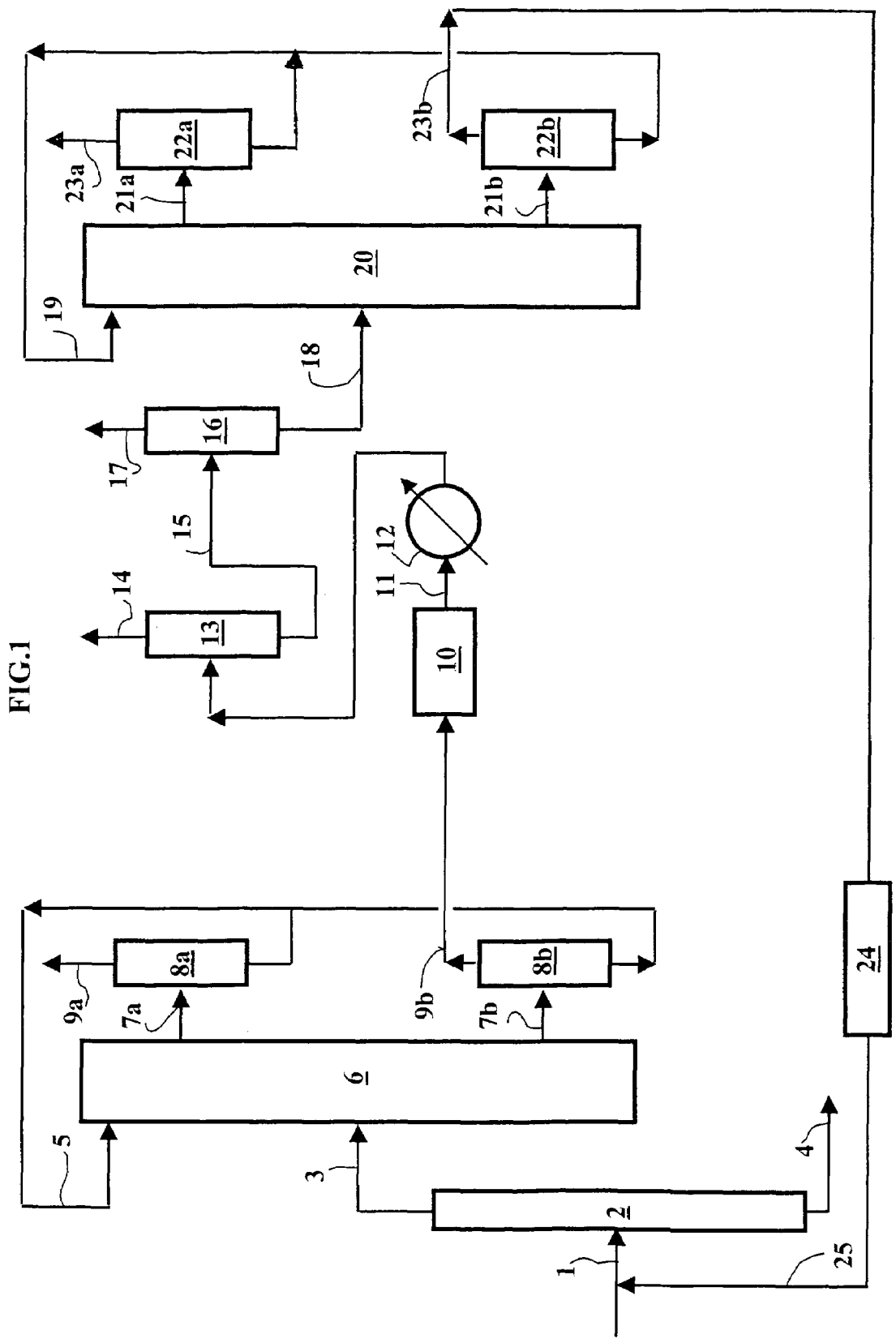
FIG. 1 shows a layout of the process in its general form.

More precisely, the invention concerns a process for co-producing para-xylene and styrene from a hydrocarbon feed containing xylenes, ethylbenzene and C9-C10 hydrocarbons, the process comprising the following steps in succession using the layout shown in FIG. 1:

a step for distilling the feed (1) carried out in a distillation column (2) to separate the xylenes, from which an overhead stream (3) comprising the major portion of the meta-xylene, para-xylene, ethylbenzene and at least a portion of the ortho-xylene is withdrawn overhead, and from which a stream (4) containing C9-C10 hydrocarbons and the remainder of the ortho-xylene is extracted from the bottom;

a step for adsorption of the overhead stream (3) carried out in at least one first adsorption column (6) operating as a simulated moving bed and containing a plurality of beds of an adsorbent, preferably interconnected in a closed loop, and having a different selectivity for para-xylene, ethylbenzene, meta-xylene and ortho-xylene, said column comprising at least four zones delimited by the point for injecting a mixture (3) containing the adsorption feed and desorbant (5), and by withdrawal points for an extract (7a) containing para-xylene, and at least one raffinate (7b) containing ethylbenzene, ortho-xylene and meta-xylene. Zone 1 for adsorbing para-xylene is located between the injection point for the desorbant (5) and the removal point for the extract (7a). Zone 2 for desorbing ethylbenzene, ortho-xylene and meta-xylene is located between the extract (7a) removal point and that for injection of the adsorption feed (3). Zone 3 for adsorption of para-xylene is located between the injection point for the feed (3) and the withdrawal point for the raffinate (7b). Zone 4 is located between the raffinate (7b) withdrawal point and that for injection of the desorbant (5);

a step for separating streams (7a) and (7b) carried out in two distillation columns (8a) and (8b) respectively supplied by withdrawals (7a) and (7b) to substantially eliminate all of the desorbant from the bottom of the column, for example. Para-xylene (9a) of at least 99.7% purity is withdrawn from the head of column (8a) and a distilled raffinate (9b) containing meta-xylene, ortho-xylene, ethylbenzene and a little para-xylene is withdrawn from the head of column (8b). The desorbant (5) is recovered from the bottom of columns 8a and 8b and is returned to the adsorption column (6);

a step for dehydrogenating ethylbenzene to styrene during which at least 50%, advantageously at least 65% by weight of the ethylbenzene introduced by stream (9b) is converted into styrene, carried out in a dehydrogenation reactor (10);

a separation step which treats the stream (11) from the preceding dehydrogenation step. The stream (11) comprises a majority of styrene, ethylbenzene, meta-xylene, ortho-xylene, para-xylene in very small quantities and other by-products in very small quantities such as toluene, benzene, ethylene, ethane, methane and hydrogen. This separation step is characterized by the use of at least one distillation column. As an example, the stream (11) is cooled in an exchanger (12) and the cooled stream (11) is sent to a separator (13) from which condensable products (15), essentially styrene, ethylbenzene, meta-xylene, para-xylene and ortho-xylene (with very small quantities of by-products benzene and toluene) are extracted from the bottom and light products (14) (ethylene, ethane, metane and hydrogen) are extracted overhead. The condensable products (15) are separated in a distillation column (16) to recover an overhead stream (17) of benzene and toluene and a tails stream (18) containing the majority of styrene, ethylbenzene, meta-xylene, ortho-xylene and a very small quantity of para-xylene;

a step for separating the mixture (18) carried out, for example, in at least one second chromatographic column (20) operating as a simulated moving bed, containing a plurality of beds of an adsorbent, preferably interconnected in a close loop and having a different selectivity for styrene, ethylbenzene, meta-xylene, ortho-xylene and para-xylene, said column (20) comprising at least four zones delimited by injections of a mixture (18) and desorbant (19), and by withdrawals of an extract (21a) containing styrene with a purity of more than 99.8%, and a raffinate (21b) containing ethylbenzene, meta-xylene, ortho-xylene, para-xylene and styrene. The first zone, for styrene desorption, is located between the desorbant (19) injection point and the extract (21a) removal point. The second zone, for desorbing ethylbenzene, meta-xylene, ortho-xylene and para-xylene, is located between the point for removing the extract (21a) and the point for injecting the adsorption feed (18). The third zone, for styrene adsorption, is located between the point for injecting the feed (18) and the raffinate (21b) withdrawal point. The fourth zone, for desorption, is located between the raffinate (21b) withdrawal point and the point for injecting desorbant (19);

a step for distilling the extract (21a) and the raffinate (21b) carried out in two distillation columns (22a) and (22b) respectively supplied by withdrawals (21a) and (21b) from the column (20) and eliminating substantially all of the desorbant (19) from the column bottom, for example. Styrene (23a) of at least 99.8% purity by weight is withdrawn overhead from the column (22a) and a distilled raffinate (23b) containing ethylbenzene, meta-xylene, ortho-xylene and para-xylene is withdrawn overhead from column (22b). The desorbant (19) is recovered from the bottom of columns (21a) and (21b) and is returned to the adsorption column (20);

an isomerization step after an optional hydrogenation step to remove styrenes is carried out in an isomerization unit (24), for the stream (23b) from column (22b), preferably carried out in the liquid phase, to re-transform the xylenes present in the stream (23b) into a stream that is enriched in para-xylene (25). This isomerised stream (25) is recycled upstream (or downstream) of the feed distillation column (2).

The process of the invention has the following advantages:

the presence of ethylbenzene in the aromatic C8 cut makes available the intermediate immediately preceding styrene in that the possibility of transforming that ethylbenzene into styrene by dehydrogenation greatly simplifies styrene production. In the majority of processes, the styrene monomer is produced from ethylbenzene itself obtained by alkylating ethylene onto benzene;

since stream (23b) is essentially composed of meta-xylene and ortho-xylene, isomerisation can advantageously be carried out in the liquid phase under substantially milder conditions than the gas phase isomerisation which would be necessitated by the presence of ethylbenzene. In fact, the quantity of ethylbenzene generally does not exceed more than 10% by weight of the isomerisation feed and preferably reaches at most 5% of the feed. The following operating conditions are given as an example: (French patent FR-A-2 792 632): a temperature of less than 300° C., preferably in the range 200° C. to 260° C.; a pressure of less than 4 MPa, preferably in the range 2 to 3 MPa; a space velocity of less than 10 h$^{-1}$, preferably in the range 2 to 4 h$^{-1}$ and a ZSM5 type catalyst;

the isomerised stream (25) is substantially free of ethylbenzene and in general represents between 60% and 80% by weight of the total flow entering the distillation column (2). The mean ethylbenzene content is thus substantially reduced, and separation by simulated moving bed in the adsorption unit (6) is thus facilitated;

the feed (1) supplying the process can have a linear and branched alkane and naphthene content of less than 1% by weight, and advantageously a naphthenes content of less than 0.3% by weight. The feed (1) supplying the process generally contains between 5% and 15% by weight of ethylbenzene. It can derive either from a unit for transalkylating C7s and C9s into xylenes, or from a catalytic unit for dismutating toluene into benzene and xylenes, or from a unit for isomerising a fluid containing ethylbenzene.

Figure 2:
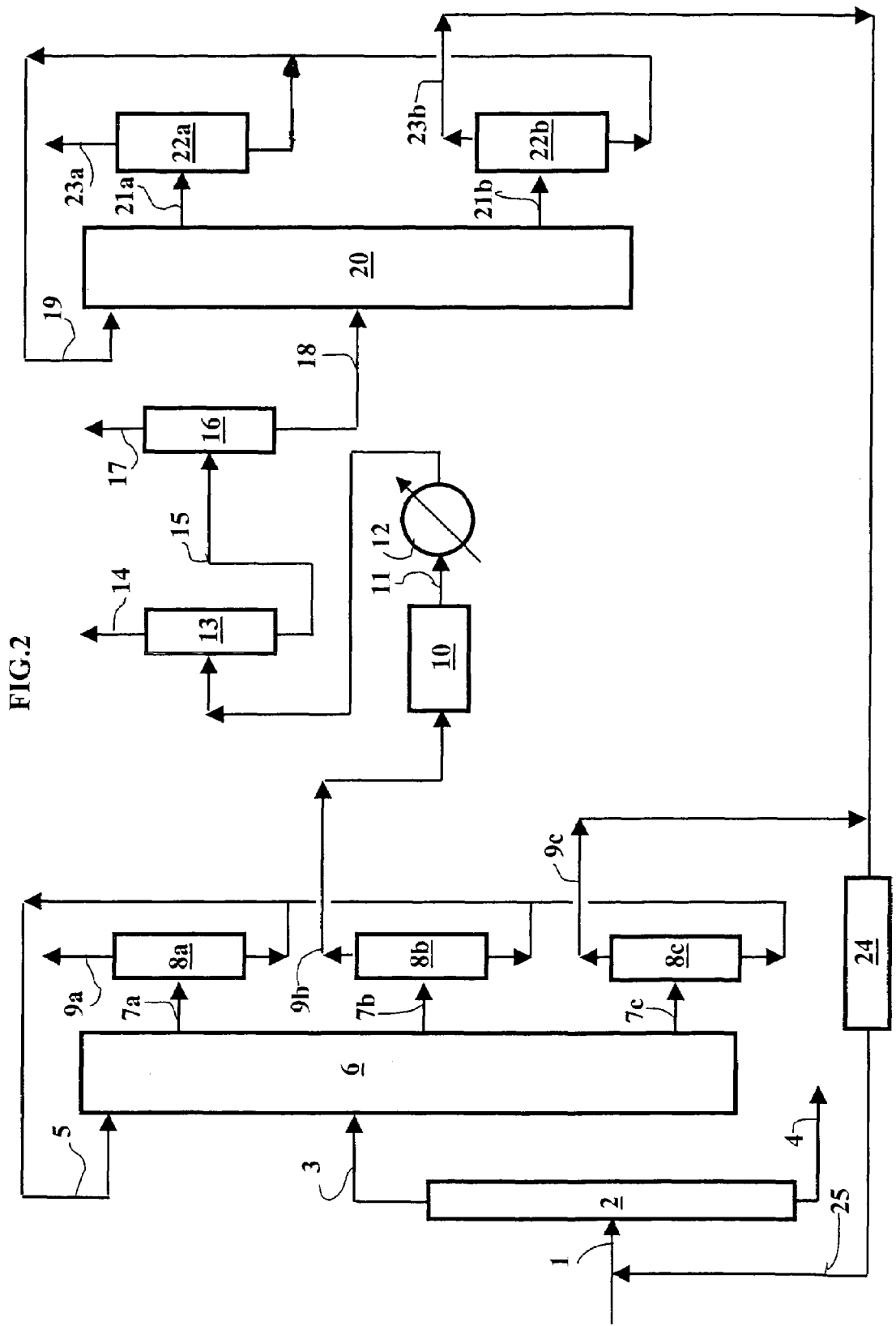
FIG. 2 shows a variation of the general layout into which a novel operating zone has been introduced into the first separation column.

In a further preferred embodiment illustrated in FIG. 2, a fifth zone can optionally be used in the separation unit (6) by withdrawing a second raffinate (7c) between the raffinate (7b) and the desorbant injection point (5). Said separation unit (6) is then characterized by the desorption zones defined above, but also advantageously by a zone 3A for adsorbing para-xylene between the point for injecting the feed and that for withdrawing the first raffinate; a zone 3B for adsorbing ethylbenzene between the point for withdrawing the first raffinate and that for withdrawing the second raffinate; and a zone 4 between the point for withdrawing the second raffinate and that for injecting the desorbant.

The column then generally contains at least 24 beds, at least 3 beds of which being in zone 3B.

The first raffinate (7b) is then enriched in ethylbenzene.

It is distilled in the distillation column (8b) to eliminate substantially all of the desorbant from the column bottom, for example. The stream (9b) withdrawn overhead is then sent to the dehydrogenation unit (10). Said second raffinate (7c) is distilled in a column (8c) to eliminate substantially all of the desorbant, the stream withdrawn overhead (9c) from the column (8c) being substantially free of ethylbenzene. Said stream (9c) is then directed to the isomerisation unit (24).

This embodiment can substantially reduce the quantity of meta-xylene and ortho-xylene which play an inert role (except in the separation unit (20)) as regards the downstream units, and unnecessarily increase the size of the units acting to produce and purify the styrene. Further, for the unit (20) for separating styrene from other $C_8$ aromatics (xylenes and ethylbenzene), the reduction in the quantity of meta- and ortho-xylene is clearly an advantage since it facilitates separation and requires less sieve to obtain a given level or purity or, for the same quantity of sieve, can increase productivity.

In a further embodiment, it is possible to provide an additional makeup of ethylbenzene deriving, for example, from a unit for alkylating ethylene onto benzene, in the stream (9b) entering the dehydrogenation unit (10).

In accordance with a further characteristic of the process, the adsorbent used in the first separation step carried out in column (6) may comprise an X zeolite exchanged with barium or a Y zeolite exchanged with potassium, or a Y zeolite exchanged with barium and potassium.

The preferred desorbant for the first separation step carried out in column (6) is para-diethylbenzene. However, other desorbants such as toluene, para-difluorobenzene or diethylbenzenes as a mixture can also be suitable.

In accordance with a further characteristic of the invention, the volume ratio of desorbant to feed in the first adsorption step carried out in column (6) can be in the range 0.5 to 2.5, preferably in the range 1.4 to 1.7.

In accordance with a further characteristic of the invention, the first adsorption step can be operated at a temperature that is generally in the range 20° C. to 250° C., preferably in the range 90° C. to 210° C., and more preferably in the range 160° C. to 200° C., and at a pressure in the range from the bubble point pressure of the xylenes at the operating temperature and 2 MPa.

The dehydrogenation step carried out in the unit (10) can be carried out with conventional ethylbenzene dehydrogenation catalysts. Any dehydrogenation reactor can be used, knowing that it is preferable to use an implementation that can reduce the energy consumption by integrating the energy recovered from the leaving effluents (11) and/or subsequent distillations as mentioned in U.S. Pat. No. 4,628,136 and U.S. Pat. No. 4,774,378.

Ethylbenzene dehydrogenation is generally carried out under the following conditions:
temperature: between 580° C. and 640° C.;
pressure: between 0.04 MPa and 0.1 MPa;
space velocity (volume flow rate of reactants per volume of catalyst): 100 to 1000 h$^{-1}$;
the catalyst used has the following composition, for example, expressed as the weight %:
$Cr_2O_3$: 8% to 28%;
SnO: 0.3% to 3.1%;
an alkali oxide (for example potassium): 0.6% to 2.8%;
silica: 0.1% to 2.8%;
the remainder being constituted by alumina.

In a preferred mode of the invention, the distillation column (16) is operated under reduced pressure, typically between 0.025 MPa and 0.035 MPa, and preferably between 0.028 MPa and 0.032 MPa, to limit the risk of styrene polymerization.

In accordance with a further characteristic of the process, in the case of using a method of separation by adsorption for the second adsorption column, the adsorbent used in the column (20) can comprise a X or Y zeolite exchanged with sodium, barium, potassium or lithium, also potassium or silver. This column can contain at least 16 beds at least 5 beds of which are in the second zone.

The preferred desorbant for the second adsorption step carried out in the column (20) can be toluene, diethylbenzenes or naphthalene, as well as their alkyl derivatives.

In accordance with a further characteristic of the invention, in the case of using a method for separation by adsorption for the second separation step, the volume ratio of desorbant to feed in the second separation step can be in the range 0.5 to 3.0, and is preferably in the range 1.4 to 2.0.

In accordance with a further characteristic of the invention, the second adsorption column can be operated at a temperature that is generally in the range 20° C. to 200° C., preferably in the range 50° C. to 150° C., and more preferably in the range 60° C. to 100° C., and at a pressure in the range from the bubble point pressure of the mixture at the selected operating temperature and 2 MPa. During said second separation step, a polymerization inhibitor can optionally be added.

In accordance with a preferred implementation of the invention, the raffinate (23b) from the second adsorption step can advantageously undergo mild hydrogenation prior to introducing it into the distillation unit (2) with the aim of saturating the vinyl group of any styrene that may be present, to prevent any deleterious pollution of the feed entering the separation unit (6). In the event that said hydrogenation is not desired, it is possible to operate the column (2) so that the styrene leaves as a tails product.

In a further variation, the size of the adsorption column can be increased for a given feed, in particular to introduce an extra bed into zone 3 to adsorb more styrene and obtain a better styrene yield. For this reason, the raffinate from this column contains substantially no more styrene.

The isomerisation step, while it can be carried out in the gas phase, is advantageously carried out in the liquid phase because of the small quantity of ethylbenzene, which will in general be at most 10% by weight and preferably at most 5% by weight of the isomerisation feed.

Liquid phase isomerisation can be carried out under the following conditions (French patent FR-A-2 792 632): a temperature below 300° C., preferably in the range 200° C. to 260° C.; a pressure of less than 4 MPa, preferably in the range 2 to 3 MPa; a space velocity of less than 10 h$^{-1}$, preferably in the range. 2 to 4 h$^{-1}$. The catalyst is zeolitic, for example ZSM5.

By way of comparison, it should be recalled that gas phase isomerisation of an effluent containing ethylbenzene is carried out under more severe conditions (see FR-A-2 792 632), namely: a temperature of more than 300° C., preferably in the range 360° C. to 480° C.; a pressure of less than 2.5 MPa, preferably in the range 0.5 to 0.8 MPa; a space velocity of less than 10 h$^{-1}$ and preferably in the range 0.5 to 6 h$^{-1}$; a mole ratio of hydrogen to hydrocarbon of less than 10 and preferably in the range 3 to 6.

In accordance with a further feature of the process, purification can be carried out by crystallizing the extract from the first separation column (6) previously freed of desorbant by distillation (8a). Crystallization is preferably carried out between +10° C. and −30° C. as described in EP-A-0 531 191 and EP-A-0 800 499, in one or more steps.

The mother liquor from crystallization can then be recycled to the supply to the simulated moving bed adsorption column (6) of the first separation zone. The solvent for washing the para-xylene crystal cake can be recycled to the supply to the simulated moving bed adsorption column (6). The washing solvent for the crystals is selected from the following solvents, for example: n-pentane, water, purified para-xylene and toluene.

In accordance with a further feature of the process, the chromatographic adsorption (and separation) column (6) can produce para-xylene, not at at least 99.7% purity with low productivity, but at least at least 50% purity with a high productivity.

The extract produced, free of desorbant, can be sent to at least one crystallization zone to deliver para-xylene crystals and a mother liquor. The para-xylene crystals are separated from the mother liquor, optionally taken up again into suspension, washed and recovered, and at least a portion of the mother liquor is recycled to the adsorption column (6).

Para-xylene crystallization, the various steps for separating the mother liquor and purification have been described, for example, in the Applicant's patents U.S. Pat. No. 6,147,272 and U.S. Pat. No. 6,111,161.

The crystals formed can be washed with suitable washing solvents; the very high purity product is recovered and the resulting washing water, which includes impurities, can be recycled to the zone for taking up into suspension.

In this manner, the productivity of the adsorption unit is maximized by relaxing the purity constraints for the para-xylene from the adsorption unit, and by ensuring the final purity of the product by employing at least one crystallization step, said purity being at least 99.7% and preferably at least 99.9% by weight.

The operating costs for the adsorption unit are minimized as it is possible to operate with a reduced number of beds and a reduced amount of solvent. Preferably, a maximum of 24 beds is used, more preferably less than 20 beds. It is also possible to minimize the quantity of desorbant by injecting it into zone 1 and by injecting the feed into zone 3 of the chromatographic column in a desorbant-to-feed volume ratio of at most 1.7, for example in a ratio in the range 0.7 to 1.5 and advantageously in the range 1.0 to 1.3.

In accordance with a further feature of the process, it is possible to operate the distillation column (2) so that at least a portion of the ortho-xylene is withdrawn from the column bottom. That stream, containing aromatics containing at least 9 carbon atoms and ortho-xylene, is then sent to a distillation column so that a stream of ortho-xylene is withdrawn overhead with a purity of at least 98.5%, and a stream containing aromatics containing at least 9 carbon atoms and possibly ortho-xylene is withdrawn from the bottom.

EXAMPLE 1

The invention will be illustrated by the following example, given by way of non limiting illustration, and made with reference to the layout of FIG. 1.

A feed with the composition of stream (1) to which a stream (25) deriving from isomerisation has just been added is sent to a separation unit constituted by a distillation column (2) with 90 plates to eliminate substantially all of the aromatics containing more than 8 carbon atoms. Stream (3) is then sent to the adsorption column (6) operating in simulated counter-current mode and having 24 beds distributed as follows:

5 beds in zone 1, 9 beds in zone 2, 7 beds in zone 3 and 3 beds in zone 4. The adsorption column (6) operated under the following operating conditions: the temperature was kept at 175° C. and the pressure at the intake of the recycling pump was maintained at 1 MPa. The adsorbent used was a hydrated BaX zeolite. The desorbant used was para-diethyl benzene used in a desorbant-feed volume ratio of 1.3.

An extract (7a) and a raffinate (7b) were withdrawn from the column (6). The extract (7a) was sent to a distillation column from which an overhead stream (9a) was withdrawn which was constituted by 99.8% pure para-xylene. The raffinate (7b) was sent to a distillation column from which an overhead stream (9b) containing 7.06% by weight of ethylbenzene was withdrawn.

This stream of ethylbenzene was sent to a dehydrogenation unit which produced a stream (18) containing 4.64% by weight of styrene after condensation and distillation.

The operating conditions for the unit for dehydrogenating ethylbenzene to styrene were as follows:
  temperature: 600° C.;
  pressure: 0.08 MPa;
  space velocity (volume flow rate of reactant per unit volume of catalyst): 300 h$^{-1}$;
  the catalyst used had the following composition by weight:
    $Cr_2O_3$: 13%
    SnO: 1.5%
    alkali oxide (for example potassium): 1%
    silica: 1%
  the remainder being constituted by alumina.

The operating conditions for the unit for mild hydrogenation of the raffinate (23b) were as follows:
  temperature: 20° C. to 200° C.;
  pressure: 0.1 to 1 MPa;
  mass flow rate of feed per unit mass of catalyst: 0.1 to 10 h$^{-1}$;

type of catalyst: comprising at least one support (for example alumina) and at least one metal from group VIII of the periodic table.

The stream (18) was sent to an adsorption column (20) operating in simulated counter current mode and having 20 beds distributed as follows: 4 beds in the first zone, 7 beds in the second zone, 5 beds in the third zone, and 4 beds in the fourth zone. The adsorption column operated under the following conditions: the temperature was kept at 100° C. and the pressure at the intake to the recycling pump was maintained at 7 bars. The adsorbent used was a NaY zeolite. The desorbant used was 1,2-dimethylnaphthalene in a volume proportion of desorbant to feed of 1.6.

An extract (21*a*) and a raffinate (21*b*) were extracted from the column (20). The extract (21*a*) was sent to a distillation unit (22*a*) from which an overhead stream (23*a*) containing 99.8% by weight of styrene was withdrawn. The raffinate (21*b*) was sent to a distillation unit (22*b*) from which an overhead stream (23*b*) was withdrawn and sent to an isomerisation unit which operated in the liquid phase at an hourly space velocity of 10 h$^{-1}$. The temperature was maintained at 200° C. and the pressure was kept at 2.5 MPa. A ZSM5 catalyst was used. The simplified material balance is shown in the table below in which the streams are referenced by a number which has the same meaning as that given FIG. 1. The composition of each stream is given in terms of the following elements as a percentage by weight Table 1):

the adsorption column (6) operating in simulated counter-current mode and having 24 beds distributed as follows: 5 beds in zone 1, 9 beds in zone 2, 5 beds in zone 3A, 3 beds in zone 3B and 2 beds in zone 4. The adsorption column (6) operated under the following operating conditions: the temperature was kept at 175° C. and the pressure at the intake to the recycling pump was maintained at 1 MPa. The adsorbent used was a hydrated BaX zeolite. The desorbant used was para-diethyl benzene used in a desorbant-feed volume ratio of 1.5.

An extract (7*a*), a raffinate (7*b*) and a second raffinate (7*c*) were withdrawn from the column (6). The extract (7*a*) was sent to a distillation column from which an overhead stream (9*a*) was withdrawn which was constituted by 99.8% pure para-xylene. The second raffinate (7*c*) was sent to a distillation column from which a stream (9*c*) was withdrawn overhead and sent to isomerisation (24). The raffinate (7*b*) was sent to a distillation column from which a stream (9*b*) containing 7.42% of ethylbenzene was withdrawn overhead. This ethylbenzene stream was sent to a dehydrogenation unit which produced (after separating the light compounds) a stream (18) containing 4.88% by weight of styrene, the remainder being constituted by $C_8$ aromatics with concentrations that are given in the table below. Dehydrogenataion was operated under the conditions of Example 1.

The stream (18) was sent to an adsorption column (20) operating in simulated counter current mode and having 20

TABLE 1

Fraction of para-xylene: PX
Fraction of meta-xylene: MX
Fraction of ortho-xylene: OX
Fraction of ethylbenzene: EB
Fraction of non aromatics: non Aro
Fraction of $C_{9+}$ aromatics: $C_9$+
Fraction of styrene: styrene

| stream n° | flow rate (g/h) | PX | MX | OX | EB | non Aro | $C_9$+ | styrene |
|---|---|---|---|---|---|---|---|---|
| 1 | 600.00 | 20.00 | 43.50 | 20.00 | 15.00 | 0.50 | 1.00 | 0.00 |
| 25 | 1644.48 | 23.283 | 50.445 | 23.283 | 1.99 | 0.00 | 1.00 | 0.00 |
| 3 | 2222.03 | 22.63 | 49.08 | 22.63 | 5.52 | 0.13 | 0.00 | 0.00 |
| 9a | 484.77 | 99.80 | 0.08 | 0.05 | 0.07 | 0.00 | 0.00 | 0.00 |
| 9b | 1734.26 | 1.10 | 62.86 | 28.98 | 7.06 | 0.00 | 0.00 | 0.00 |
| 11 | 1734.26 | 1.10 | 62.86 | 28.98 | 1.33 | 0.00 | 0.00 | 4.58 |
| 18 | 1714.38 | 1.11 | 63.59 | 29.32 | 1.34 | 0.00 | 0.00 | 4.64 |
| 23a | 76.31 | 0.005 | 0.10 | 0.06 | 0.035 | 0.00 | 0.00 | 99.80 |
| 23b** | 1644.48 | 1.16 | 66.29 | 30.56 | 1.99 | 0.00 | 0.00 | 0.00 |

**Composition after mild hydrogenation of styrene remaining in the raffinate under the following conditions:
temperature: 150° C.
pressure: 0.6 MPa
mass flow rate of feed per unit mass of catalyst: 1 h$^{-1}$
catalyst: $Al_2O_3$
Ni: 0.3% by weight.

EXAMPLE 2

The invention will also be illustrated by the following example, given by way of non limiting illustration, and made with reference to the layout of FIG. 2. the stream numbers shown in the Table below have the same meanings as those appearing in FIG. 2.

A feed with the composition of stream (1) to which stream (25) deriving from isomerisation has just been added is sent to a separation unit constituted by a distillation column (2) with 90 plates to eliminate substantially all of the aromatics containing more than 8 carbon atoms. Stream (3) is then sent to beds distributed as follows: 4 beds in the first zone, 7 beds in the second zone, 5 beds in the third zone and 4 beds in the fourth zone. The adsorption column operated under the following conditions: the temperature was kept at 120° C. and the pressure at the intake to the recycling pump was kept at 1 MPa. The adsorbent used was a NaY zeolite. The desorbant used was toluene used in a desorbant-feed volume ratio of 1.6.

An extract (21*a*) and a raffinate (21*b*) were withdrawn from column (20). The extract (21*a*) was sent to a distillation column (22*a*) from which an overhead stream (23*a*) containing 99.8% by weight of styrene was withdrawn. The raffinate (21*b*) was sent to a distillation unit (22*b*) from which an overhead stream (23b) was withdrawn overhead and sent to an isomerisation unit which was operated under the following conditions: the temperature was kept at 200° C. and the pressure was kept at 2.5 MPa. The catalyst was of the ZSM5 type, with an HSV of 10 h$^{-1}$.

TABLE 1

| stream n° | flow rate (g/h) | PX fraction | MX fraction | OX fraction | EB fraction | C$_9$+ fraction | styrene fraction |
|---|---|---|---|---|---|---|---|
| 1 | 600.00 | 20.00 | 44.00 | 20.00 | 15.00 | 1.00 | 0.00 |
| 25 | 1643.18 | 24.39 | 52.42 | 21.85 | 1.35 | 0.00 | 0.00 |
| 3 | 2237.17 | 23.28 | 50.30 | 21.41 | 5.01 | 0.00 | 0.00 |
| 9a | 506.10 | 99.80 | 0.13 | 0.056 | 0.014 | 0.00 | 0.00 |
| 9b | 1492.30 | 0.96 | 64.27 | 27.35 | 7.42 | 0.00 | 0.00 |
| 9c | 238.77 | 0.54 | 69.36 | 29.52 | 0.58 | 0.00 | 0.00 |
| 18 | 1474.31 | 0.97 | 65.05 | 27.69 | 1.41 | 0.00 | 4.88 |
| 23a | 69.90 | 0.005 | 0.10 | 0.06 | 0.035 | 0.00 | 99.80 |
| 23b* | 1404.41 | 1.02 | 68.28 | 29.06 | 1.63 | 0.00 | 0.00 |

*This composition was determined after hydrogenation of the remaining styrene in the raffinate under the conditions of Example 1.

The invention claimed is:

1. A process for coproduction of high purity paraxylene and styrene, starting from a feedstock containing xylenes, ethylbenzene and C9-C10 hydrocarbons, the process comprising the following successive steps:

a feedstock (1) distillation step so as to separate xylenes, performed in a distillation column (2), from which is withdrawn, at the head, a stream (3) comprising most of the metaxylene, paraxylene, ethylbenzene and at least part of the orthoxylene, and from which is withdrawn, at the bottom, a stream (4) containing C9-C10 hydrocarbons, the remaining part is orthoxylene;

a step of subjecting head stream (3) to adsorption in at least a first adsorption column (6) operating as a simulated moving bed and containing numerous adsorbent beds, optionally interconnected in a closed loop, and having a different selectivity for paraxylene, ethylbenzene, metaxylene, and orthoxylene, said column comprising at least four operating zones: a first zone for desorption of paraxylene located between the injection point of a desorbent (5) and the removal point of an extract (7a), a second zone for desorption of ethylbenzene, orthoxylene and metaxylene located between the removal point of extract (7a) and the injection point of adsorption feedstock (3), a third zone for adsorption of paraxylene, located between the injection point of adsorption feedstock (3) and withdrawal of a raffinate product (7b) and a fourth zone, located between the withdrawal point of raffinate product (7b) and the injection point of desorbent (5);

a step of distillation of extract (7a), performed in at least one distillation column (8a), from which is withdrawn substantially pure paraxylene (9a), on the one hand, and on the other hand desorbent, which is then recycled, at least in part, in the first adsorption column;

a step of distillation of raffinate product (7b) in at least one distillation column (8b) from which is withdrawn, on the one hand, desorbent that is recycled at least in part in the first adsorption column and, on the other hand, a distilled raffinate product (9b) containing metaxylene, orthoxylene, and a minor amount of ethylbenzene compared to the xylenes;

a step of dehydrogenation of the distilled raffinate product containing metaxylene, orthoxylene and ethylbenzene to obtain an effluent containing styrene, metaxylene, orthoxylene, unconverted ethylbenzene and by-products, performed in at least one dehydrogenation zone (10), during which at least 50% by weight of the ethylbenzene introduced is converted into styrene;

at least one step of eliminating by-products from said effluent in at least one distillation column, to produce a mixture (18) containing mostly styrene, ethylbenzene, metaxylene, and orthoxylene;

a step of separating mixture (18), in which a first stream (23a) containing styrene with a purity of at least 99.8% by weight is produced and a second stream (23b) containing mostly metaxylene and orthoxylene is produced; and an isomerization step, in a unit (24), of second stream (23b), optionally in liquid phase, in at least one isomerization zone, at the end of which a stream (25) containing paraxylene, orthoxylene, and metaxylene are recovered and are recycled upstream to feedstock distillation column (2).

2. Process according to claim 1, wherein the step of separating mixture (18) is performed in at least a second adsorption column (20) operating as a simulated moving bed, containing numerous beds of an adsorbent, preferably interconnected in a closed loop and having different selectivity for styrene, ethylbenzene, metaxylene, and orthoxylene, said column (20) comprising at least four chromatographic zones: a first zone, for desorption of styrene, located between the injection point of a desorbent (19) and that of the removal of an extract (21a); a second zone, for desorption of ethylbenzene, metaxylene, and orthoxylene, located between the point where extract (21a) is removed and where an adsorption feedstock comprising said mixture (18) is injected; a third zone, for adsorption of styrene, located between the injection point of feedstock (18) and that of the withdrawal of a refined product (21b), and a fourth zone located between the point of withdrawal of raffinate product (21b) and that of injection of desorbent (19).

3. A process according to claim 1, wherein the extract is distilled to eliminate desorbent from it, the raffinate product is distilled to eliminate desorbent from it, and the recovered desorbent is recycled at least in part to the second adsorption column.

4. A process according to claim 1, wherein first adsorption column (6) is operated in five operating zones, a first raffinate product (7b), enriched with ethylbenzene, is withdrawn from this column and a second raffinate product (7c) is withdrawn between the withdrawal point of first raffinate product (7b) and the injection point of desorbent (5), said adsorption column (6) being then characterized in that it comprises: said operating zones 1 and 2 of first adsorption column (6), a zone 3A for adsorption of paraxylene, located between the feedstock injection point and the withdrawal point of the first raffinate product, a zone 3B for adsorption of ethylbenzene, located between the withdrawal point of the first raffinate product and the withdrawal point of the second raffinate product, a zone 4 located between the withdrawal point of the second raffinate product and the desorbent injection point.

5. A process according to claim 4, wherein first raffinate product (7b) is distilled in a distillation column (8b) to eliminate from it substantially all the desorbent, first distilled raffinate product (9b) being then conveyed to dehydrogenation zone (10), and second raffinate product (7c) being then distilled in a distillation column (8c) to eliminate from it substantially all the desorbent, second distilled raffinate product (9c), which is recovered substantially free of ethylbenzene, being then directed toward the isomerization zone.

6. A process according to claim 1, wherein the adsorbent used in the first adsorption column is an X zeolite exchanged at barium, or a Y zeolite exchanged at potassium, or a Y zeolite exchanged at barium and potassium.

7. A process according to claim 2 in which the adsorbent used in the second adsorption column is an X or Y zeolite exchanged at sodium or barium or potassium or lithium as well as at potassium and silver.

8. A process according to claim 1, wherein the desorbent of the first adsorption column is selected from the group formed by paradiethylbenzene, toluene, paradifluorobenzene and diethylbenzenes in mixture.

9. A process according to claim 2, wherein the desorbent of the second adsorption column is selected from the group formed by toluene, naphthalene, and its alkylated derivatives.

10. A process according to claim 2, wherein the volumetric ratio of desorbent to feedstock for the first adsorption column is between 0.5 and 2.5, and the volumetric ratio of desorbent to feedstock for the second adsorption column by adsorption is between 0.5 and 3.0.

11. A process according to claim 1, wherein the first adsorption step is performed at a temperature between 20° C. and 250° C., and under a pressure between the boiling pressure of xylenes at the operating temperature and 2 MPa.

12. A process according to claim 2, wherein the second adsorption column is operated at a temperature between 20° C. and 200° C. and under a pressure between the boiling pressure of the mixture at the operating temperature and 2 MPa.

13. A process according to claim 4, wherein the first adsorption column contains at least 24 beds, at least 3 of which are in zone 3B.

14. A process according to claim 2, wherein the second adsorption column contains at least 16 beds, at least 5 of which are in the second zone.

15. A process according to claim 1, wherein fraction (9a) is enriched with paraxylene, to at least 50% by weight of purity, and is conveyed to at least one crystallization zone to deliver paraxylene crystals and a mother liquor, the crystals are separated from the mother liquor, optionally resuspended, washed, and recovered, and the mother liquor is recycled in the first separation column.

16. A process according to claim 1, wherein distillation column (2) is operated so that at least part of a fraction containing orthoxylene is withdrawn at the bottom of the column, said fraction further containing aromatics with at least 9 carbon atoms is conveyed to a distillation column so that an orthoxylene stream with a purity of at least 98.5% by weight is withdrawn at the head and a stream containing aromatics with at least 9 carbon atoms and possibly orthoxylene is withdrawn at the bottom.

17. A process according to claim 1, wherein the separation step of mixture (18) is conducted by a separation technique selected from the group formed by distillation, azeotropic distillation, extractive distillation, liquid-liquid extraction, chemical complex formation, membrane separation, and their combination.

18. A process according to claim 1, wherein second stream (23b) further contains styrene, this stream is hydrogenated in a hydrogenation zone, and a hydrogenation effluent is recovered and conveyed to the isomerization zone.

19. A process according to claim 1, wherein second stream (23b) contains at most 10% by weight of ethylbenzene and the isomerization (24) is conducted in the liquid phase.

20. A process according to claim 19, wherein said second stream 23(b) contains at most 5% by weight of ethylbenzene.

21. A process according to claim 19, wherein the isomerised stream (25) represents 60-80% by weight of the total flow to the distillation column 2.

22. A process according to claim 1, wherein said minor amount of ethylbenzene is about 7% by weight.

23. A process for coproduction of high purity paraxylene and styrene, starting from a feedstock containing xylenes, ethylbenzene and C9-C10 hydrocarbons, the process comprising the following successive steps:

a feedstock (1) distillation step so as to separate xylenes, performed in a distillation column (2), from which is withdrawn, at the head, a stream (3) comprising most of the metaxylene, paraxylene, ethylbenzene and at least part of the orthoxylene, and from which is withdrawn, at the bottom, a stream (4) containing C9-C10 hydrocarbons, the remaining part is orthoxylene;

a step of subjecting head stream (3) to adsorption in at least a first adsorption column (6) operating as a simulated moving bed and containing numerous adsorbent beds, optionally interconnected in a closed loop, and having a different selectivity for paraxylene, ethylbenzene, metaxylene, and orthoxylene, said column comprising at least four operating zones: a first zone for desorption of paraxylene located between the injection point of a desorbent (5) and the removal point of an extract (7a), a second zone for desorption of ethylbenzene, orthoxylene and metaxylene located between the removal point of extract (7a) and the injection point of adsorption feedstock (3), a third zone for adsorption of paraxylene, located between the injection point of adsorption feedstock (3) and withdrawal of a raffinate product (7b) and a fourth zone, located between the withdrawal point of raffinate product (7b) and the injection point of desorbent (5);

a step of distillation of extract (7a), performed in at least one distillation column (8a), from which is withdrawn substantially pure paraxylene (9a), on the one hand, and on the other hand desorbent, which is then recycled, at least in part, in the first adsorption column;

a step of distillation of raffinate product (7b) in at least one distillation column (8b) from which is withdrawn, on the one hand, desorbent that is recycled at least in part in the first adsorption column and, on the other hand, a distilled raffinate product (9b) containing metaxylene, orthoxylene, and a minor amount of ethylbenzene compared to the xylenes;:

a step of dehydrogenation of the distilled raffinate product containing metaxylene, orthoxylene and ethylbenzene to obtain an effluent containing styrene, metaxylene, orthoxylene, unconverted ethylbenzene and by-products, performed in at least one dehydrogenation zone (10), during which at least 50% by weight of the ethylbenzene introduced is converted into styrene;

at least one step of eliminating by-products from said effluent in at least one distillation column, to produce a mixture (18) containing mostly styrene, ethylbenzene, metaxylene, and orthoxylene;

a step of separating mixture (18) in at least a second adsorption column (20) operating as a simulated moving bed, in which a first stream (23a) containing styrene with a purity of at least 99.8% by weight is produced and a second stream (23b) containing mostly metaxylene and orthoxylene is produced; and an isomerization step, in a unit (24), of second stream (23b), optionally in liquid phase, in at least one isomerization zone, at the end of which a stream (25) containing paraxylene, orthoxylene, and metaxylene are recovered and are recycled upstream to feedstock distillation column (2).

24. A process as in claim 23 wherein said step of dehydrogenation of the distillation raffinate product is performed in at least one dehydrogenation zone (10) without the addition of steam.

25. A process as in claim 23 wherein said step of dehydrogenation of the distillation raffinate product is performed in at least one dehydrogenation zone (10) with a catalyst free of iron oxide.

26. A process as in claim 23 wherein said step of dehydrogenation of the distillation raffinate product is performed in at least one dehydrogenation zone (10) with a catalyst free of chlorine.

27. A process as in claim 25 wherein the catalyst used in at least one dehydrogenation zone (10) comprises tin and chromium.

* * * * *

UNITED STATES PATENT AND TRADEMARK OFFICE
CERTIFICATE OF CORRECTION

PATENT NO. : 7,592,499 B2
APPLICATION NO. : 10/666523
DATED : September 22, 2009
INVENTOR(S) : Wolff et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 422 days.

Signed and Sealed this

Twenty-first Day of September, 2010

David J. Kappos
*Director of the United States Patent and Trademark Office*